United States Patent [19]
Lu et al.

[11] Patent Number: 6,096,528
[45] Date of Patent: Aug. 1, 2000

[54] THERMOTOLERANT AND HIGH ACETIC ACID-PRODUCING *ACETOBACTER* BACTERIUM

[75] Inventors: Shu-Fen Lu; Fwu-Ling Lee; Han-Ken Chen, all of Hsin-chu, Taiwan

[73] Assignee: Food Industry Research and Development, Hsin-Chu, Taiwan

[21] Appl. No.: 09/370,784

[22] Filed: Aug. 5, 1999

[30] Foreign Application Priority Data

Jul. 19, 1999 [TW] Taiwan .................................. 88112354

[51] Int. Cl.$^7$ ............................... C12N 1/20; C12P 7/54; C07C 53/08; C07C 53/10
[52] U.S. Cl. ......................... 435/252.1; 435/140; 562/607
[58] Field of Search .................................. 435/140, 252.1

[56] References Cited

U.S. PATENT DOCUMENTS 4,654,306  3/1987  Entani et al. ............................ 435/253

OTHER PUBLICATIONS

Lu S.F. et al. "A Thermotolerant and High Acetic Acid–Producing Bacterium Acetobacter sp. I14–2." Society for Applied Microbiology (1999) Vo. 86, pp. 55–62.

De Ley, J. et al. "Family VI. Acetobacteraceae" In Bergey's Manual of Systematic Bacteriology vol. 1, pp. 267–278, (1984).

Swings, J. "The genera Acetobacter and Gluconobacter". In The Prokaryotes vol. III, pp. 2268–2286. (1991).

Nakayama, T. "Studies on Acetic Acid Bacteria". Journal of Biochemistry 49, pp. 158–163, (1961).

Lotong, N. et al. "Production of Vinegar by Acetobacter Cells Fixed on a Rotation Disc Reactor". Applied Microbiology and Biotechnology 32. pp. 27–31. (1989).

Yamada, Y. et al. "The Cellular Fatty Acid Composition In Acetic Acid Bacteria". Journal of General Applied Microbiology 27, pp. 405–417. (1981).

Saeki, A. "Application of Gluconobacter Oxydans Subsp. Sphaericus IFO 12467 to Vinegar Production". Journal of Fermentation and Bioengineering 7, pp. 232–234. (1993).

Asai, T. et al. "The Flagellation and Taxonomy of Genera Gluconobacter and Acetobacter with Reference . . . ". Journal of General Applied Microbiology 10, pp. 95–126. (1964).

Steele, D.B. et al. "Production of low–molecular–weight, alkaline–active, thermostable protease by a novel, . . . ". Enzyme Microbial Technology 14, pp. 358–360. (1992).

Akagawa Matsushita, M. et al. "Isoprenoid quinone composition of some marine Alteromonas, . . . ". Journal of General Applied Microbiology 138, pp. 2275–2281, (1992).

Tamaoka, J. et al. "Determination of DNA base composition by reversed–phase high–performance liquid chromatography" FEMS Microbiology Letters 25, pp. 125–128, (1984).

Ezaki, T. et al. "Fluorometric Deoxyribonucleic Acid–Deoxyribonucleic Acid Hybridization in Microdilution . . . ". International Journal of Systematic Bacteriology 39, pp. 224–229, (1989).

Gillis, M. et al. "Acetobacter diazotrophicus sp. Nov., a Nitrogen–Fixing Acetic Acid Bacterium". International Journal of Systematic Bacteriology 39, pp. 361–364, (1989).

Pecina, R. et al."High–Performance Liquid Chromatographic Elution Behaviour of Alcohols, Aldehydes, Ketones, Organic Acids . . . ". Journal of Chromatography 287, pp. 245–258 (1984).

Sievers, M. et al. "Acetobacter Europaeus sp. Nov., a Main Component of Industrial Vinegar Fermenters in Central Europe" Systematic Applied Microbiology 15, pp. 386–392. (1992).

*Primary Examiner*—Francisco Prats
*Assistant Examiner*—Susan D. Coe
*Attorney, Agent, or Firm*—Ladas & Parry

[57] ABSTRACT

The present invention relates to a thermotolerant bacterium, designated as Acetobacter sp. I14-2, with high production of acetic acid which was isolated from spoiled banana in Taiwan. The present invention also relates to compositions containing the new species and methods for acetic acid production.

14 Claims, 5 Drawing Sheets

THERMOTOLERANT AND HIGH ACETIC ACID-PRODUCING ACETOBACTER BACTERIUM

BACKGROUND OF THE INVENTION

Industrial vinegar production is usually conducted by means of microbial fermentation. Acetic acid bacteria, in particular, contribute to the generation of acetic acid in vinegar fermentation. Acetic acid bacteria were classified into two genera, Acetobacter and Gluconobacter, depending upon their abilities to over-oxidize acetate or lactate and the positions of their flagella (De Ley et al., Family VI. Acetobacteraceae. In *Bergey's Manual of Systematic Bacteriology* Vol. 1, pp. 267–278. Baltimore: Williams & Wilkins, 1984). Since Acetobacter prefers oxidizing ethanol instead of glucose for producing acetic acid but Gluconobacter prefers to the contrary, most strains useful in vinegar manufacture belong to Acetobacter, whereas Gluconobacter is used for industrial applications, such as fermentation of ketoglucomic acid, sorbose and dihydroxyacetone (Swings, The genera Acetobacter and Gluconobacter. In *The Prokaryotes* Vol. III, pp. 2268–2286, New York: Springer Verlag, 1991). Among the Acetobacter species, *Acetobacter aceti, Acetobacter pasteurianus, Acetobacter polyoxogenes* and *Acetobacter europaneus* are the most popular strains for making acetic acid in vinegar factories on the grounds that their oxidization of ethanol is superior and they hardly destroy acetic acid later (U.S. Pat. No. 4,654,306; Sievers et al., *Systematic Applied Microbiology* 15, 386–392, 1992).

Most bacteria useful for acetic acid production are mesophilic strains with optimum temperature for growth at about 30° C. These strains are neither capable of growing at temperatures above 30° C. nor producing acetic acid when they are cultured at temperatures higher than 32° C. (Nalayama, *Journal of Biochemistry* 49, 158–163, 1961). This sensitivity to elevated temperature brings a limitation to most industrial vinegar production which is not strictly controlled at 30° C. In recent years, the temperature in summer has gradually elevated in many tropical and subtropical countries. As an example in Taiwan, the average indoor temperature at nights during the summer is above 30° C. Therefore, a majority of local vinegar manufacture is limited to a great extent for almost half a year. As far as those critical factors of vinegar production are concerned, an ideal bacterial strain should possess high efficiency of acetic acid production as well as remarkable tolerance to intermediates and products in considerable amounts which are generated during fermentation, such as ethanol and acetic acid.

Some efforts have been made to improve the bacterial properties which are advantageous in vinegar industry, such as increased acetic acid production rate and enhanced tolerance to high acetic acid, ethanol and fermentation temperature (Lotong el al., *Applied Microbiology and Biotechnology* 32, 27–31, 1989).

However, there is still a need in the vinegar industry to identify a new acetic acid-producing strain having versatile advantages, including thermotolerance, resistance to ethanol and high acetic acid productivity. In particular for vinegar industry in tropical and subtropical areas, there is still a need of a thermotolerant strain capable of propagating and producing acetic acid at a temperature above 30° C.

SUMMARY OF THE INVENTION

The present invention relates to a novel species of bacterium useful in acetic acid fermentation and, more particularly, to a novel thermotolerant species of bacterium named Acetobacter sp. I14-2 for use in producing acetic acid in a fermentation process.

It is an objective of the present invention to provide the species of acetic acid-producing bacterium for producing acetic acid in a fermentation process with high productivity, i.e. Acetobacter sp. I14-2, and a mutant or variant thereof.

Another objective of the present invention is to provide the species of acetic acid-producing bacterium having activity for producing acetic acid at a temperature above 30° C.

It is yet another objective of the present invention to provide a composition of matter comprising the acetic acid-producing bacterium for storage, acetic-acid production and other purposes.

Yet another objective of the present invention is to provide a method for producing acetic acid comprising employing Acetobacter sp. I14-2, or its mutant or variant, as an inoculant in a fermentation process and incubating the bacterium under the conditions appropriable for said Acetobacter sp. I14-2 generating of acetic acid.

DETAILED DESCRIPTION OF THE INVENTION

Figure 1:
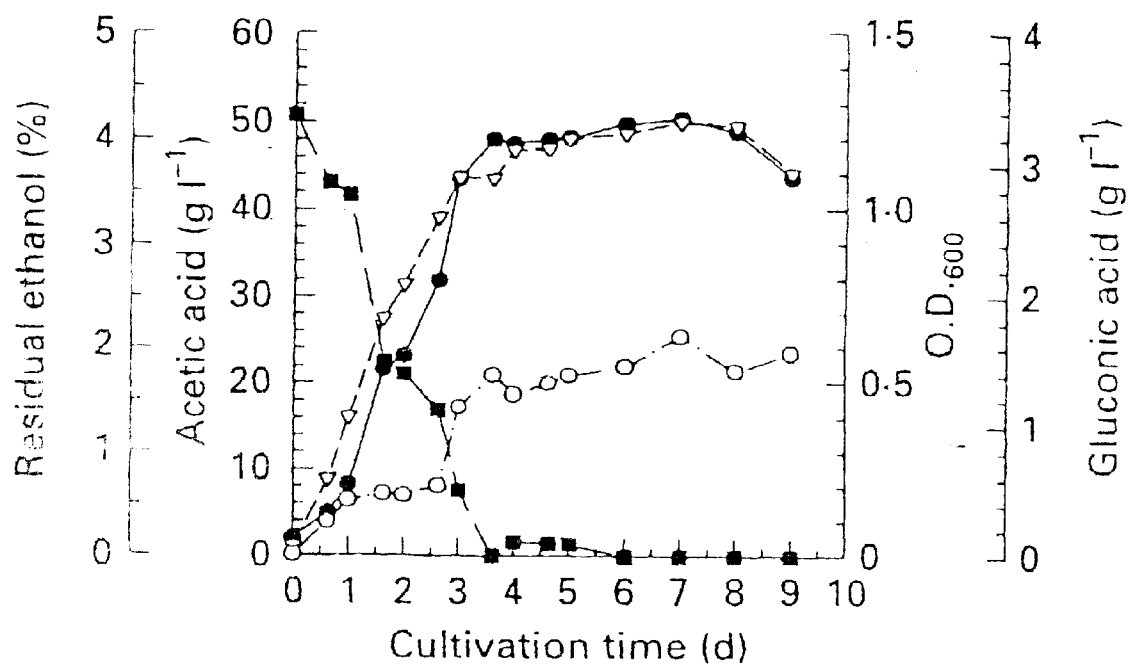
FIG. 1 is a diagram showing time courses of acetic acid and gluconic acid production in relation to cell growth of Acetobacter sp. I14-2. Ethanol (■); acetic acid (●); gluconic acid (○); O.D.$_{600}$ (▽).

The present invention relates to a novel species of bacterium useful in acetic acid fermentation. In particular, the present invention relates to a novel thermotolerant species of bacterium for use in producing acetic acid with high productivity.

According to the invention, a preliminary investigation for acetic acid-producing strains was conducted. Among many local samples taken from fresh fruits, flowers, rotten fruits, soils, wine with dregs and wood of fruit trees in Taiwan, some possible strains of interest were then isolated and then purified to obtain the pure cultures thereof. The acetic acid-producing isolates were obtained (see below Example 1, Table 1). Among the thirteen isolates, an isolate named I14-2 was notably prominent due to its very high productivity of acetic acid.

The isolate I14-2 were characterized, see below Example 2 (Table 2). The isolate I14-2 was gram-negative, aerobic and acidophilic rod which oxidizes ethanol to acetic acid.

The isolate I14-2 has a high resistance to both ethanol and acetic acid and is capable of producing acetic acid at a temperature above 30° C., as well as oxidizing acetate and lactate. When incubated as a static culture, the isolate I14-2 did not form a pellicle on the liquid surface, but generated aggregates suspended in the culture.

As for the cellular fatty acid composition of the isolate I14-2, it contained a straight-chained and unsaturated fatty acid, C18:1 as the major component (51.71%) and a small amount of a straight-chained and saturated fatty acid C14:0, which is an important characteristic of the Acetobacter genus (Yamada et al., *Journal of General Applied Microbiology* 27, 405–417, 1981). The ubiquinone system of this isolate was $Q_9$ ($Q_8$), and guanine plus cytosine content (GC content) of DNA was determined to be 51.7 mol %.

Based on the phenotypic and cytological characteristics of the isolate I14-2, the isolate belong to the genus Acetobacter, but has some distinctive properties from a number of known species under the same genus. As shown in the comparison of the DNA homologies between the isolate I14-2 and the known Acetobacter species (i.e., *Acetobacter aceti* NCIMB 8621 and *Acetobacter pasteurianus* NCIMB 12228), the two reference strains shared only 3% and 56% homology with the isolate I14-2, respectively. This indicated the distinctive differences between the isolate I14-2 and the two known strains. Given the above the isolate I14-2 exhibited major phenotypic characteristics as typically found in known Acetobacter sp. but species-specific distinctions from known species. Therefore, the isolate I14-2 according to the present invention was concluded as a novel species of Acetobacter and designated as Acetobacter sp. I14-2.

The isolate I14-2 was deposited under the Budapest Treaty with the China Center for Type Culture Collection (CCTCC) on Jul. 16, 1999, under accession No. CCTCC M 99007. The new species according to the present invention has the biological characteristics of the CCTCC deposit.

According to the disclosure herein, persons skilled in the art will be able to discover or prepare a mutant or variety of Acetobacter sp. I14-2 by means of traditional screening or artificial manipulation known in the art, such as selections under a stress (e.g., a temperature or a chemical agent) or mutagenesis (e.g., using chemical, physical or biological agents). Therefore, mutants or variants of Acetobacter sp. I14-2 also fall within the scope of the present invention.

The Acetobacter sp. I14-2 was surprisingly found to be capable of producing acetic acid in a fermentation with high productivity. The preferred temperature of the fermentation process is above 20° C. Acetobacter sp. I14-2 was also surprisingly found to be capable of producing acetic acid at a temperature above 30° C.

With the advantages of thermotolerance, high acetic acid productivity and resistance to ethanol, Acetobacter sp. I14-2 of the invention is very useful in the fermentation production of vinegar having high acetic acid concentration, preferably at a temperature above 20° C., more preferably at a temperature above 30° C.

The present invention also provides a method of producing acetic acid comprising employing Acetobacter sp. I14-2, or a mutant or variant thereof, as an inoculant in a fermentation process and incubating the bacterium under the conditions appropriate for said Acetobacter sp. I14-2 generating acetic acid. Due to the property of thermotolerance of the novel bacterium of the present invention, it will be possible a strict condition at a temperature of 30° C. for a fermentation process is not required. No special conditions are demanded in the fermentation production of vinegar, such as white vinegar, using the novel bacterial species of the present invention. Operational conditions and other details for a fermentation process would be commonly available for persons skilled in the art.

As Acetobacter sp. I14-2 exhibits considerable resistance to ethanol and prefers oxidizing ethanol to obtain acetic acid, an adequate amount of ethanol is preferably added during fermentation according to the present invention. The adequate amount the ethanol is preferably below 10% v/v, more preferably around 5% v/v.

The present invention also provides a composition of matter comprising Acetobacter sp. I14-2. For example, the composition of matter may contain Acetobacter sp. I14-2, conditioned medium and other microbes, which are collected from a fermentation process. The composition may be employed for subsequent fermentation processes. In another aspect, the composition of matter may be a culture suited for cryopreservation, which may contain Acetobacter sp. I14-2 in, e.g., a nutrient medium plus glycerol. In a further aspect, the composition of matter may contain Acetobacter sp. I14-2 and other bacteria known as useful in a fermentation process, e.g., for vinegar production. The composition of matter may further contain microbes which are known to be capable of bringing a unique flavor or taste for the fermentation products (e.g., vinegar) or enhancing the properties thereof.

All patents and publications cited herein are incorporated by reference.

EXAMPLES

The following examples illustrate various aspects of the present the present invention but do not limit the claims in any manner whatsoever.

Example 1
Isolation of Acetic Acid-Producing Bacteria

Among eighty-six samples including 35 from fresh fruits, 24 from flowers, 14 from rotten fruits, six from soils, five from wine with dregs and two from the wood of fruit trees, some acetic acid-producing bacteria were isolated. The bacteria were first enriched in an enrichment medium at 30° C. with shaking in a rotary shaker at 150 rpm for 3–5 days. The enrichment medium contained: potato dextrose broth (Difico), 110 g/L; peptone, 3 g/L; yeast extract, 5 g/L; ethanol, 5 g/L; acetic acid, 0.3 g/L; pH 4.2. The colonies with acid production, which was indicated by the formation of a clear zone around the cells on AC screening medium, were isolated. The AC medium consisted of all the components of enrichment medium except acetic acid and was modified by adding: $CaCO_3$, 5 g/L; agar, 20 g/L. All isolates were preliminarily characterized by morphology and cellular fatty acid composition. Sixty-nine isolates of acetic acid-producing bacteria were obtained, 21 from fresh fruits, 11 from flowers, 28 from rotten fruits, one from soil, three from wine with dregs and five from the wood of fruit trees.

For evaluation of acetic acid production, the isolates were grown in 10 ml of seed medium for 2 days, and 1.5 ml of the liquid cultures were taken and transferred to 50 ml of fresh seed medium, and incubated at 30° C. with shaking at 150 rpm for 2 days. A medium modified from Saeki (*Journal of Fermentation and Bioengineering* 7, 232–234, 1993) was used as seed medium, which contained: glycerol, 5 g/L; dextrose, 5 g/L; polypeptone (WaKo), 5 g/L; yeast extract, 5 g/L; ethanol, 20 g/L; acetic acid, 2 g/L; pH 4.3. The main culture was prepared by inoculating 1 ml of the second seed culture into a medium containing: glycerol, 2 g/L; dextrose, 30 g/L; polypeptone (Wako), 2 g/L; yeast extract, 2 g/L; ethanol, 50 g/L; acetic acid, 2 g/L; pH4. 1 and shaking at 50 rpm for 3 days. The culture was centrifuged at 4° C. and 13000 g for 15 minutes, and the supernatant fluid was collected to determine the amounts of acetic acid, ethanol and gluconic acid. The growth of the bacteria was determined with the absorbance of the culture broth at 600 nm using a spectrophotometer (DU 640, Beckman, Palo Alto, Calif., USA). As to the capability of oxidizing ethanol to acetic acid, the data of the tested isolates are given in Table 1. All isolates were tested in the medium containing 5% (v/v) ethanol and incubated at 30° C. with shaking at 150 rpm for 3 days before analysis. Some reference Strains: Acetobacter aceti IFO 3283, Acetobacter aceti DSM 2002, Acetobacter pasteurianus ATCC 9432, Acetobacter pasteurianus ATCC 6438 and Acetobacter sp. CCRC 12326 were isolated from vinegar and used for comparison.

TABLE 1

Acetic Acid Production from Ethanol Reference

| Reference strains and new isolates | Acetic acid (g/L) | Ethanol (%) | Gluconic acid (g/L) |
|---|---|---|---|
| Acetobacter aceti IFO 3283 | 23.0 | 1.68 | 1.14 |
| Acetobacter aceti DSM 2002 | 14.0 | 2.80 | 1.76 |
| Acetobacter pasteurianus ATCC 9432 | 6.1 | 3.17 | 0.35 |
| Acetobacter pasteurianus ATCC 6438 | 13.3 | 2.83 | 0.91 |
| Acetobacter sp. CCRC 12326 | 15.2 | 2.80 | 0.81 |
| I4-4 | 24.8 | 1.93 | 0.38 |
| I8-1 | 23.1 | 2.06 | 0.43 |
| I10-3 | 30.3 | 1.35 | 0.72 |
| I14-2 | 43.6 | 0.39 | 1.26 |
| I16-2 | 25.8 | 2.01 | 0.59 |
| I21-2 | 24.4 | 1.87 | 1.74 |
| I34-2 | 25.4 | 1.88 | 1.04 |
| I40-1 | 26 | 1.59 | 0.52 |
| I41-1 | 31.1 | 1.48 | 0.42 |
| I42-1 | 33.6 | 1.24 | 0.69 |
| I48-1 | 28.7 | 1.66 | 0.52 |
| I48-3 | 32.5 | 1.38 | 2.41 |
| I56-2 | 24.5 | 2.08 | 0.47 |

Acetobacter aceti IFO 3283, an excellent bacterium for vinegar production (Saeki 1993, supra), produced 23 g/L acetic acid after incubation for 3 days in this study. Six of the isolates produced acetic acid at higher levels than all the reference strains, and seven isolates were capable of oxidizing ethanol to the levels similar to or better than that of Acetobacter aceti IFO 3283. The isolate I14-2, with the highest acetic acid productivity and ethanol consumption rate, was chosen for further studies. Acetic acid productivity of this isolate was twice that of Acetobacter aceti IFO 3283. The isolate I14-2 was obtained from spoiled banana collected at Talichung, Taiwan.

Example 2
Taxonomic Studies on Isolate I14-2
2.1. Methodologies
2.1.1 Phenotypic Characteristics
The morphological characteristics of the isolate I14-2 were determined by the conventional method (De Ley et al 1984, supra). Ninety-five carbon source utilization patterns of the isolate were determined using a rapid identification system, Biolog MicroStation™ (Biolog, Inc., Calif., USA) (Fredrickson el al., Applied and Environmental Microbiology 57, 402–411, 1991). To examine the oxidation of acetate and lactate, the isolate was cultivated in a medium containing 2 g/L sodium acetate or sodium lactate and 0.02 g/L bromothymol blue at 30° C. for 5–7 days (Asai et al, Journal of General Applied Microbiology 10, 95–126, 1964).

2.1.2. Cellular Fatty Acid Composition

Cellular fatty acid composition of the isolate was analyzed using the MIDI Microbial Identification System (Microbial ID, Inc., Del., USA). The cells were grown on trypticase soy broth (BBL) containing 20 g/L agar at 30° C. for 24 hours, harvested, and lysed according to the manufacturer's instructions to prepare methyl esters of cellular fatty acids. The esters were analyzed by gas chromatography according to the method of Steele et al. (Enzyme Microbial Technology 14, 358–360, 1992).

2.1.3. Isoprenoid Quinones

Isoprenoid quinones of the isolate were extracted with chloroform-methanol (2:1, v/v) and purified by thin layer chromatography (TLC) on silica gel 60F 254 (Merck, 20×20 cm) using benzene as developing solvent. Quinones recovered from the TLC plates were dissolved in acetone and analyzed by high performance liquid chromatography (HPLC) as described by Akagawa-Matsushita et al. (Journal of General Applied Microbiology 138, 2275–2281, 1992) with minor modification. The HPLC system was equipped with a reversed-phase column (Nova-Pak C18, 3.9×150 mm, Waters, Milford, Mass., USA), and a mixture of methanol and isopropanol (2:1, v/v) was used as the mobile phase at 1 ml/min flow rate. Types of quinone were identified by absorption at 275 nm and comparison with standards.

2.1.4. DNA Base Composition and DNA Homology

Fresh cells were harvested from AC broth after incubation for 2 days and digested with lysozyme and protease K at 37° C. for 1 hour. Bacterial DNA was isolated and purified using the Qiagen Genomic DNA Kit (Qiagen Inc., Germany). The molar percentage of guanosine plus cytosine of chromosomal DNA was determined by HPLC (Tamaoka et al., FEMS Microbiology Letters 25, 125–128, 1984). DNA homologies between the isolate and Acetobacter type strains were determined according to the method of Ezaki et al (International Journal of Systematic Bacteriology 39, 224–229, 1989).

2.2. Results

Selected phenotypic and chemotaxonomic characteristics of this isolate are shown in Table 2.

TABLE 2

Selected Phenotypic and Chemotaxonomic Characteristics of Isolate I14-2

Phenotypic characteristics

1. Rod-shaped
2. Gram-negative
3. Motility: negative
4. Anaerobic growth: negative
5 Catalase: positive
6. Oxidase: negative
7. Lactate oxidation: positive
8. Acetate oxidation: positive
9. Assimilation of carbon sources

| Carbon Sources | Assimilation |
|---|---|
| α-D-glucose, D-arabitol, D-fructose, D-galactose, methyl pyruvate, acetic acid, formic acid, γ-hydroxy butyric acid, D-/L-lactic acid, bromo | positive |

TABLE 2-continued

Selected Phenotypic and Chemotaxonomic Characteristics of Isolate I14-2

| | |
|---|---|
| succinic acid, L-alanine and glycerol L-arabinosee, D-mannose, maltose, D-mannitol, N-acetyl-D-glucosamine, L-fucose, D-trehalose, dextrin, glycogen, adonitol, phenylacetate, cellobiose, α-lactose, L-rhamnose, D-raffinose, turanose, D-glucnose, malate, caprate, citrate, adipate, succinic acid, psicose and sucrose | negative |

| Cellular fatty acid composition | |
|---|---|
| 1. C18:1 | 51.71% |
| 2. C19:0 cyclo | 16.30% |
| 3. C16:0 | 12.47% |
| 4. C14:0 2OH | 5.74% |
| 5. C16:0 2OH | 4.37% |
| 6. C18:0 | 2.69% |
| 7. C14:0 | 2.43% |
| 8. C16:0 3OH | 1.87% |
| 9. C16:1 iso | 1.26% |
| 10. C20:3 | 1.15% |

| | |
|---|---|
| Quinone | $Q_9$ ($Q_8$) |
| G + C content of DNA | 51.7 mol % |
| DNA homology with | |
| Acetobacter aceti NCIMB 8621 | 3% |
| Acetobacter pasteurianus NCIMB 12228 | 56% |

From the results of studies on the ability to oxidize acetate and lactate, two important characteristics for differentiating Acetobacter from Gluconobacter were found. The results suggested that the isolate I14-2 belong to the genus Acetobacter. This isolate contained a straight-chained and unsaturated fatty acid C18:1 as the major component and a small amount of a straight-chained and saturated fatty acid C14:0, which is an important characteristic of the genus Acetobacter (Yamada et al. 1981, supra). This result indicated that the isolate I14-2 is an Acetobacter strain. In order to identify the isolate, quinone type, G+C content of DNA, and DNA homology were determined. The isolate I14-2 contained $Q_9$ as a major quinone and $Q_8$ as a minor quinone. The isolate distinguishes from *Acetobacter liquefaciens, Acetobacter xylinum, Acetobacter diazotrophicus* and *Acetobacter methanolicum* (Gillis et al., *International Journal of Systematic Bacteriology* 39: 361–364, 1989). The G+C content of DNA of the isolate I14-2 was 51.7 mol 1%. The quinone type and the G+C content of DNA of the isolate I14-2 were close to those of *Acetobacter aceti* and *Acetobacter pasteurianus*. Using these two Acetobacter type strains, *Acetobacter aceti* NCIMB 8621 and *Acetobacter pasteurianus* NCIMB 12228, as probes, the isolate I14-2 exhibited low levels (3.0 and 55.7%) of DNA homology with the strains NCIMB 8621 and NCIMB 12228, respectively. Based on the above results, the isolate I14-2 was a new species that is genetically distinct from previously described Acetobacter species. Therefore, this isolate should be a new Acetobacter species and was designated as Acetobacter sp. I14-2.

The Acetobacter sp. I14-2 was deposited under the Budapest Treaty with the China Center for Type Culture Collection (CCTCC) on Jul. 16, 1999 under accession No. CCTCC M 99007.

Example 3
Acetic and Gluconic Acids Assay 3.1. Methodologies

Acetic acid production of the isolate was assayed according to the method of Pecina et al (*Journal of Chromatography* 287, 145–258, 1984). A BioRad (Hercules, Calif., USA) Aminex HPX-87H column was used in the HPLC system and maintained at 40° C., and 5 mmol/L $H_2SO_4$ was used as the mobile phase with a flow rate of 0.6 ml/min. Acetic acid and ethanol in the eluate were detected and quantified by monitoring with an RI detector. Gluconic acid produced by the isolate was evaluated by HPLC with two connecting Shodex (Showa Denko Co., Tokyo, Japan) KC 811 columns maintained at 40° C.; 5 mmol/L $HClO_4$ was used as the mobile phase with a flow rate of 1.0 ml/min. A reagent containing 0.2 mmol/L bromothymol blue in 15 mmol/L $Na_2HPO_4$ was used to separate organic acid components, and gluconic acid was detected with the absorbance at 445 nm. Samples were mixed with 100 μl of 200 g/L sulphosalicylic acid and centrifuged at 9000 g for 10 min before analysis.

3.2. Results

In the time course study of acetic acid production from ethanol by the isolate I14-2, it was found that the accumulation of acetic acid paralleled the cell growth (FIG. 1). The lag period for acetic acid production by Acetobacter sp. I14-2 was not obvious (within 12 hours), while the lag period for the cell growth was not observed. Ethanol was consumed steadily until cell growth reached stationary phase after 3.5-day cultivation, whereupon the accumulation reached a maximum level of about 50 g/L. It was found that gluconic acid formation occurred during the log phase along with the accumulation of acetic acid. A further production was not found during the stationary phase.

Example 4
Effects of Initial Acetic Acid on Acetic Acid Production

Figure 2:
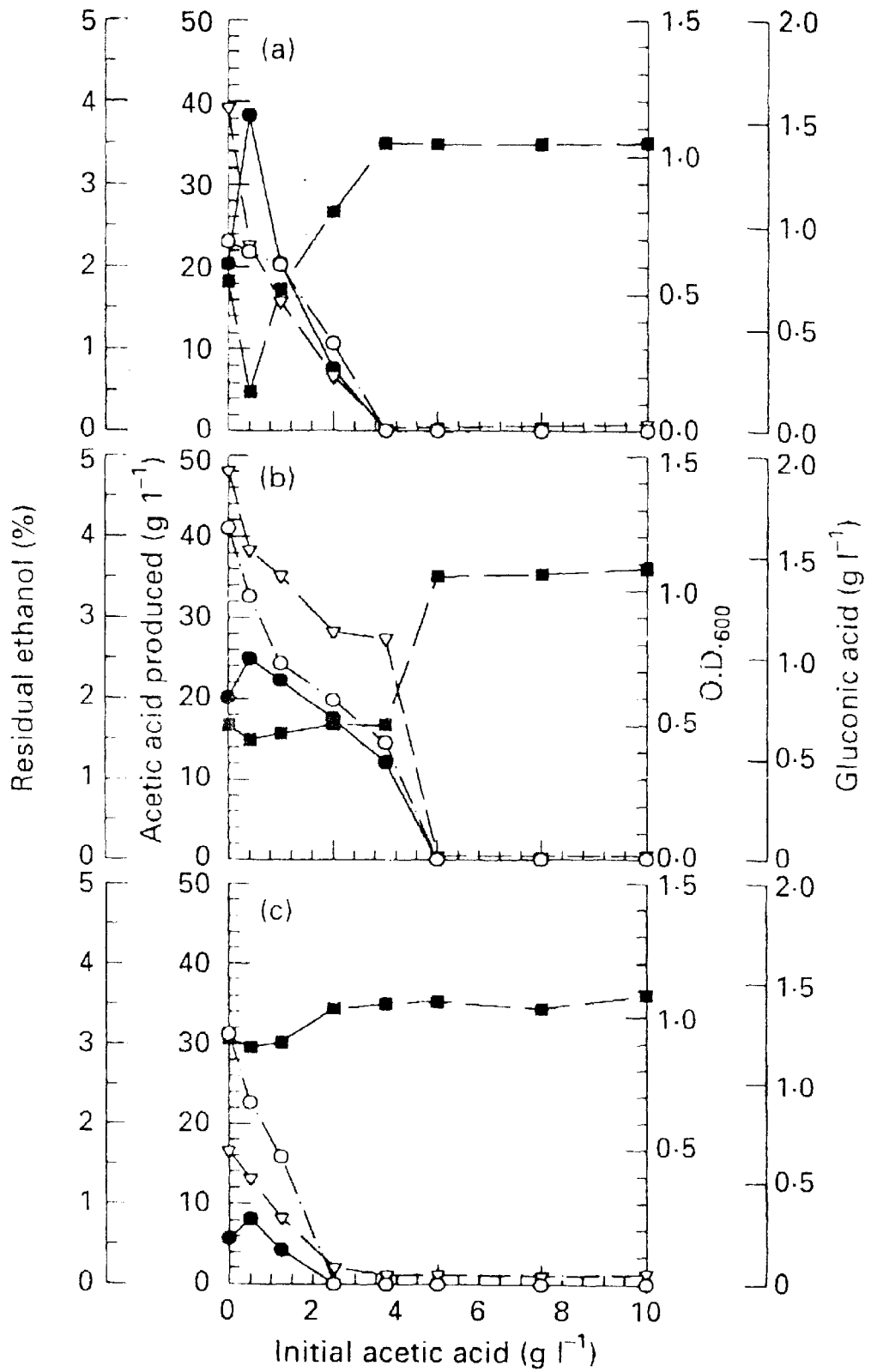
FIG. 2 is a diagram showing effect of initial acetic acid concentration on acetic acid production. Acetobacter sp. I14-2 (a); *Acetobacter aceti* IFO 3283 (b); Acetobacter sp. CCRC 12326 (c); residual ethanol (■); acetic acid (●); gluconic acid (○); O.D.$_{600}$ (▽).

The effect of acetic acid on acetic acid production was studied, Acetobacter sp. I14-2 were inoculated in the media containing the different amounts of acetic acid ranging from 0 to 40 g/L, respectively. Acetic acid was added to the culture medium at a concentration of 0, 2, 5, 10, 15, 20, 30 or 40 g/L, giving an initial pH value of 5.44, 3.71, 3.44, 3.22, 3.11, 3.01, 2.93 or 2.83. Acetic acid production by the isolate I14-2 reached the highest of 38 g/L at an initial concentration of 2 g/L, which is similar in trend to the results of *Acetobacter aceti* IFO 3283 and Acetobacter sp. CCRC 12326 but with the different levels of accumulation (FIG. 2). This isolate produced the same amount of acetic acid as it did in a medium without the addition of acetic acid. At an initial acetic acid concentration of 10 g/L, the isolate I14-2 retained about 20% of its maximal activity of producing acetic acid at 2 g/L (FIG. 2a), while *Acetobacter aceti* IFO 3283 retained about 68% (FIG. 2b) and Acetobacter sp. CCRC 12326 was inactivated (FIG. 2c). At an initial acetic acid concentration of 15 g/L, only *Acetobacter aceti* IFO 3283 retained about 50% of its maximal activity of acetic acid production. Gluconic acid production by these three strains was the inhibited steadily by increasing initial acetic acid concentration. This indicated that the formation of gluconic acid was repressed either by an acetic acid added initially and produced during fermentation, or by low pH caused by acetic acid.

Example 5
Effect of Initial Ethanol Concentration on Acetic Acid Production

Figure 3:
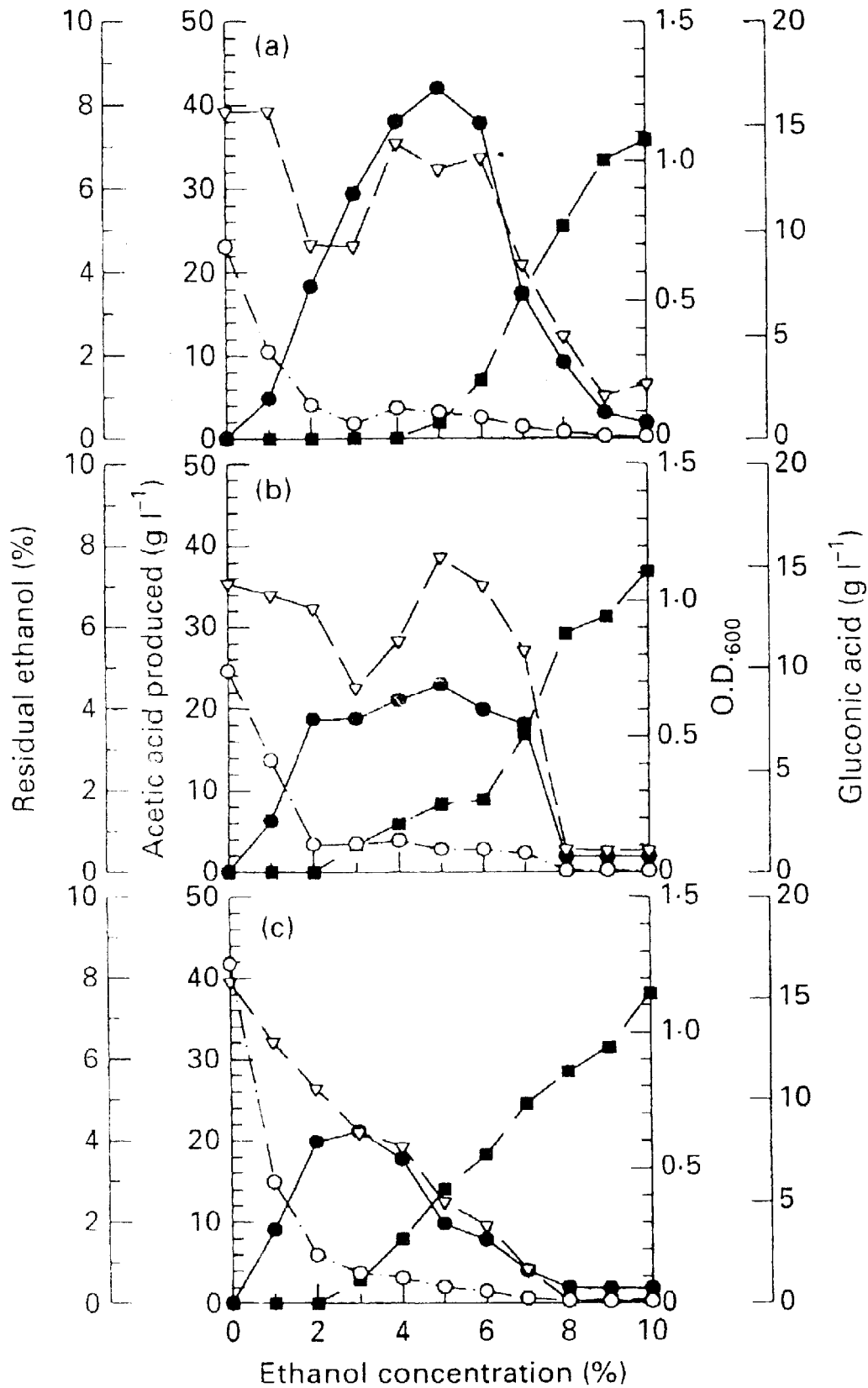
FIG. 3 is a diagram showing effect of initial ethanol concentration on acetic acid production. Acetobacter sp. I14-2 (a); *Acetobacter aceti* IFO 3283 (b); Acetobacter sp. CCRC 12326 (c); residual ethanol (■); acetic acid (●); gluconic acid (○); O.D.$_{600}$ (▽).

The effect of ethanol concentration on acetic acid production was studied by incorporating 0–10% (v/v) ethanol in the media. The acetic acid produced by the isolate I14-2 showed an almost symmetrical profile over a range of initial ethanol concentration of 0–10% with a peak at 5% (FIG. 3a). At the initial ethanol concentrations of 1–5%, the amounts of acetic acid produced by the isolate increased in proportion to the initial ethanol concentrations, while the amounts of gluconic acid produced decreased with the initial ethanol concentrations. At initial ethanol concentrations of 5–10%, the amounts of acetic acid produced by the isolate decreased in proportion to the initial ethanol concentrations, while the amount of gluconic acid produced remained low. At the peak at 5% ethanol, Acetobacter sp. I14-2 produced about 44 g/L of acetic acid, which is twice that produced by *Acetobacter aceti* IFO 3283 at the same ethanol concentration (FIG. 3*b*), but the amounts of gluconic acid produced by both strains were almost the same. The optimum ethanol concentration for acetic acid production was 5% for both the isolate I14-2 and *Acetobacter aceti* IFO 3283, as well as 3% for Acetobacter sp. CCRC 12326 (FIG. 3*c*). The production of gluconic acid, a product oxidized from glucose, by the three strains reached the highest level in a medium without ethanol addition. This suggests that Acetobacter would oxidize glucose to gluconic acid when ethanol is absent, but would prefer utilizing ethanol to glucose when ethanol is present. In addition to a higher acetic acid productivity, the isolate I14-2 exhibited a higher ethanol tolerance than the two reference strains. This isolate was still active in the presence of 9% ethanol (FIG. 3*a*). The tolerance to ethanol of mesophilic strains such as the two reference strains is lower than 8% ethanol. The relative activities of Acetobacter sp. I14-2 for producing acetic acid at 8% and 9% ethanol were about 22% and 7.3%, respectively, compared with that at 5% of ethanol.

Example 6
Effect of Temperature on Acetic Acid Production

Figure 4:
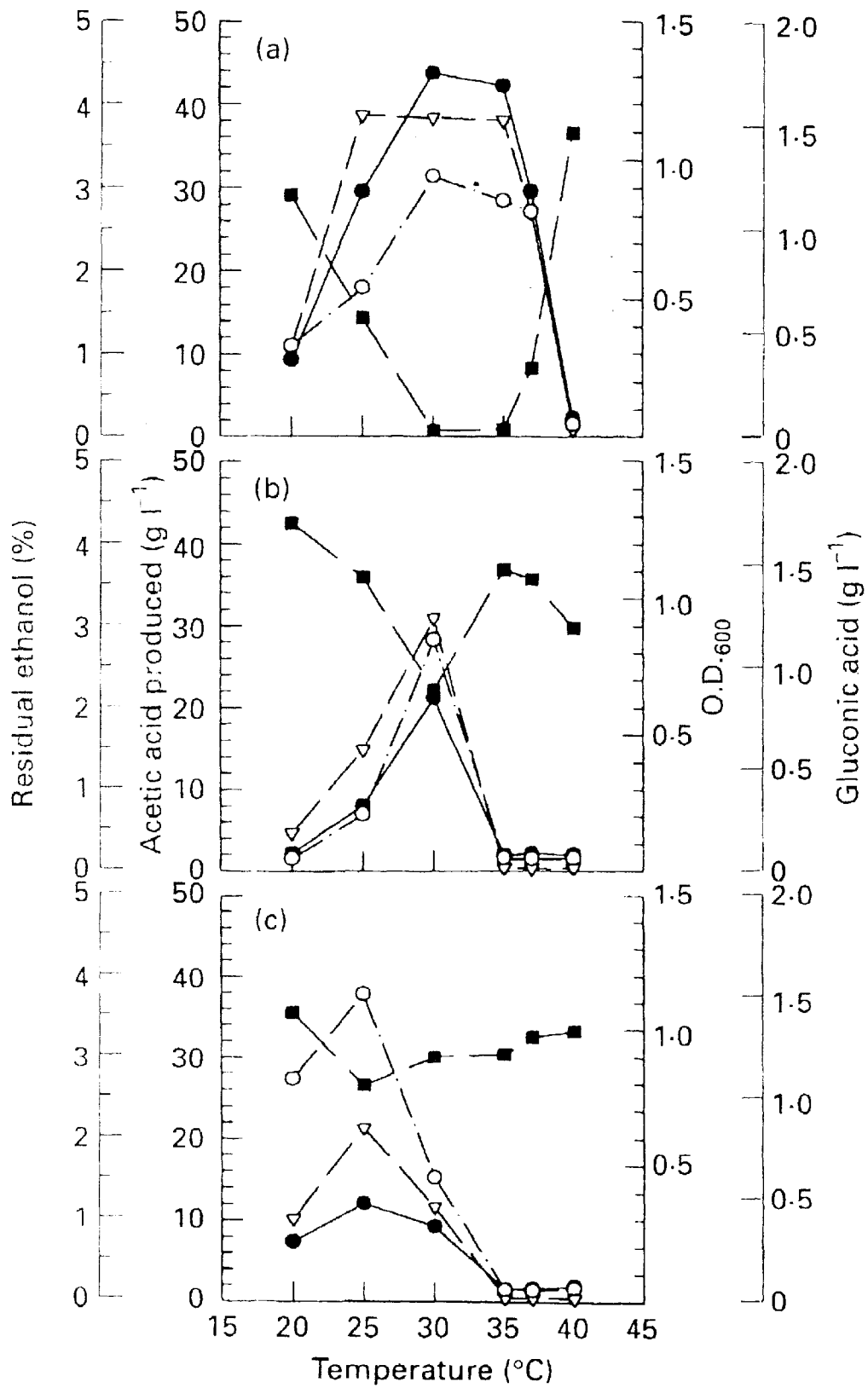
FIG. 4 is a diagram showing effect of temperature on acetic acid production. Acetobacter sp. I14-2 (a); *Acetobacter aceti* IFO 3283 (b); Acetobacter sp. CCRC 12326 (c); residual ethanol (■); acetic acid (●); gluconic acid (○); O.D.$_{600}$ (▽).

The optimum temperature of acetic acid production was determined. The isolate was incubated at various temperatures for 3 days, and the residual activity of acetic acid production in each sample was compared with the control sample cultured at 30° C. Acetic acid was produced by Acetobacter sp. I14-2 at a temperature ranging from 20° C. to 37° C. with an optimum at 30° C. (FIG. 4*a*). The 3-day acetic acid productivity was measured as 97% and 68% at 35° C. and 37° C., respectively, compared with that at 30° C. To the contrary, *Acetobacter aceti* IFO 3283 and Acetobacter sp. CCRC 12326 did not grow or produce acetic acid when incubated at 35° C. A optimum temperature for acetic acid production of 30° C. and 25° C., respectively, was found (FIGS. 4*b* and 4*c*). The effects of temperature on gluconic acid production and cell growth were coincident in trend with acetic acid formation.

Figure 5:
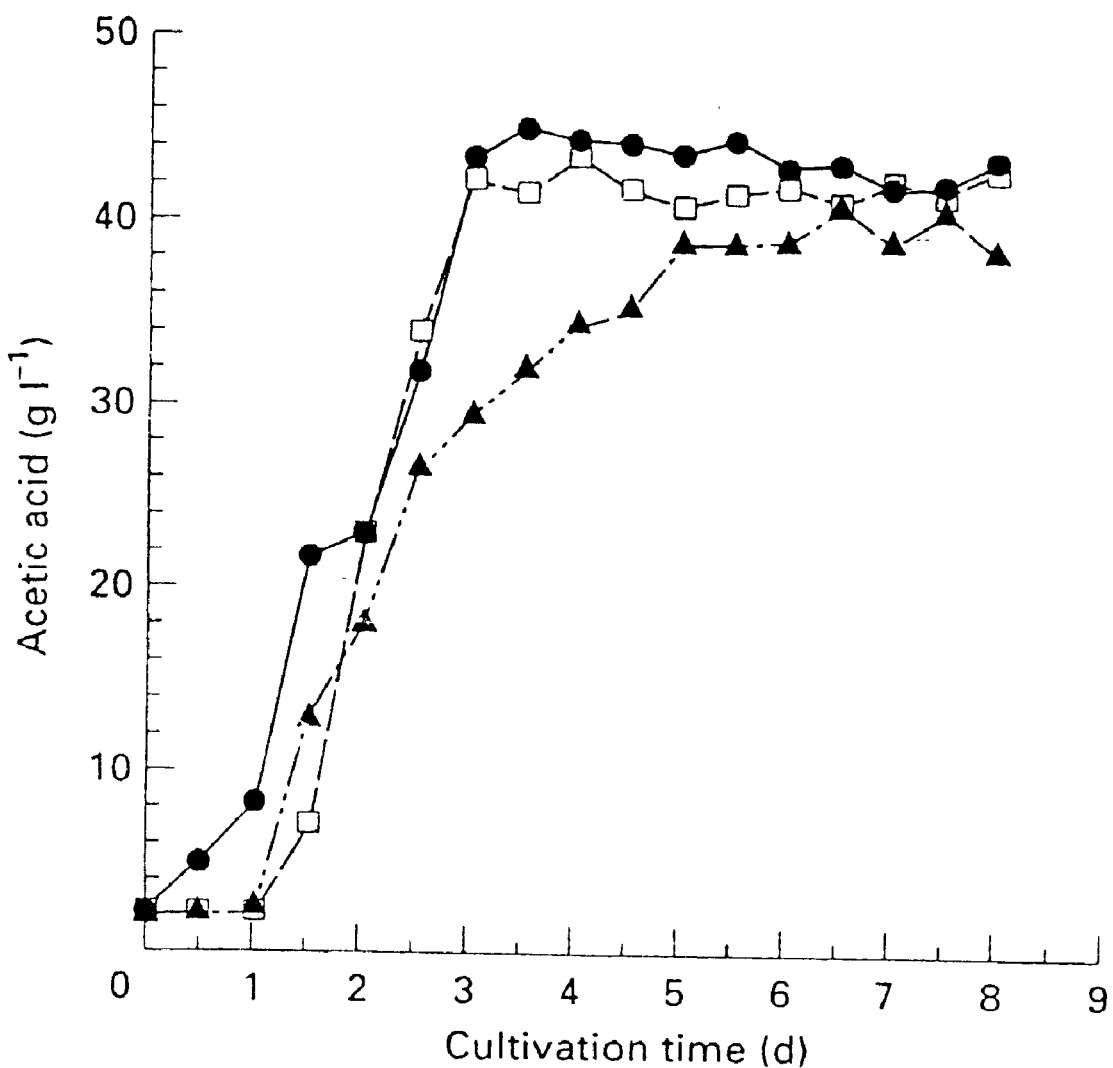
FIG. 5 is a diagram showing time course of acetic acid production from ethanol by Acetobacter sp. I14-2 at various temperatures. 30° C. (●); 35° C. (□); 37° C. (▲).

When the temperature was raised, a delay in ethanol oxidation was observed. The lag period for acetic acid production from ethanol by Acetobacter sp. I14-2 was prolonged to about 24 hours at 35° C. and 37° C. (FIG. 5). However, ethanol was completely exhausted in 3–4 days and acetic acid production reached almost the same maximum level when incubated at both 30° C. and 35° C. Further, Acetobacter sp. I14-2 exhibited an outstanding thermotolerance with a yield of 85% and 82% when cultured at 35° C. and 37° C., respectively, for 6 days. Although the consumption of ethanol at 37° C. was obviously delayed, the isolate I14-2 could produce 41 g/L of acetic acid. The amount of acetic acid produced might decreased due to ethanol volatilization at a higher temperature.

The examples provided above are not meant to be exclusive. Many other variations and modifications of the above described embodiments of the present invention would be carried out without departing from the spirit and scope of this invention.

What is claimed is:

1. An isolated, pure culture of Acetobacter sp. I14-2 or a mutant or variant thereof.

2. The bacterium according to claim 1 capable of producing acetic acid in a fermentation process at a temperature above 20° C.

3. The bacterium according to claim 1 capable of producing acetic acid in a fermentation process at a temperature above 30° C.

4. The bacterium according to claim 1 having the biological characteristics of the bacterium deposited with the CCTCC on Jul. 16, 1999 under the accession No. CCTCC M 99007.

5. A composition of matter comprising Acetobacter sp. I14-2, or a mutant or variant thereof.

6. The composition of matter according to claim 5 as a seed culture.

7. The composition of matter according to claim 5 for use in vinegar fermentation.

8. The composition of matter according to claim 7 wherein the fermentation is at a temperature over 20° C.

9. The composition of matter according to claim 7 wherein the fermentation is at a temperature over 30° C.

10. A method of producing acetic acid comprising employing Acetobacter sp. I14-2, or a mutant or variant thereof, as an inoculant in a fermentation process and incubating the bacterium under the conditions appropriate for said Acetobacter sp. I14-2 generating acetic acid.

11. The method according to claim 10, wherein the bacterium is incubated at a temperature over 20° C.

12. The method according to claim 10, wherein the bacterium is incubated at a temperature over 30° C.

13. The method according to claim 10, wherein ethanol is added at the beginning of the fermentation.

14. The method according to claim 13, wherein the amount of ethanol is below 10% v/v.

* * * * *